(12) United States Patent
Ratjen et al.

(10) Patent No.: US 8,926,558 B2
(45) Date of Patent: Jan. 6, 2015

(54) MEDICAMENT DELIVERY DEVICE WITH MIXING MECHANISM

(75) Inventors: Jochen Ratjen, Nacka (SE); Anders Holmqvist, Värmdö (SE); Martin Karlsson, Göteborg (SE)

(73) Assignee: SHL Group AB, Nacka Strand (SE)

( * ) Notice: Subject to any disclaimer, the term of this patent is extended or adjusted under 35 U.S.C. 154(b) by 827 days.

(21) Appl. No.: 13/002,354

(22) PCT Filed: Jun. 5, 2009

(86) PCT No.: PCT/EP2009/056918
§ 371 (c)(1),
(2), (4) Date: Mar. 23, 2011

(87) PCT Pub. No.: WO2010/000559
PCT Pub. Date: Jan. 7, 2010

(65) Prior Publication Data
US 2011/0251553 A1 Oct. 13, 2011

(30) Foreign Application Priority Data
Jul. 4, 2008 (SE) ...................................... 0801613

(51) Int. Cl.
*A61M 37/00* (2006.01)
(Continued)

(52) U.S. Cl.
CPC ........... *A61M 5/2066* (2013.01); *A61M 5/2033* (2013.01); *A61M 5/2448* (2013.01);
(Continued)

(58) Field of Classification Search
CPC ........... A61M 5/2033; A61M 5/2066; A61M 5/2448; A61M 5/326; A61M 2005/2073; A61M 2005/2451; A61M 2210/0618
USPC ................ 604/131, 90, 82–89, 136–137, 218
See application file for complete search history.

(56) References Cited

U.S. PATENT DOCUMENTS 6,793,646 B1 * 9/2004 Giambattista et al. .......... 604/90

7,402,150 B2 * 7/2008 Matsumoto et al. ............ 604/90
(Continued)

FOREIGN PATENT DOCUMENTS

| DE | 10 2006 017209 A1 | 10/2007 |
| EP | 0288443 A1 | 10/1988 |
| EP | 0562671 A1 | 9/1993 |
| WO | 2006/080893 A1 | 8/2006 |

OTHER PUBLICATIONS

EPO, Int'l Search Report in PCT/EP2009/056918, Oct. 22, 2009.
EPO, Written Opinion in PCT/EP2009/056918, Oct. 22, 2009.

*Primary Examiner* — Theodore Stigell
(74) *Attorney, Agent, or Firm* — Piedmont Intellectual Property

(57) ABSTRACT

A medicament delivery device comprising a housing (10; 110); a medicament container holder (12; 120) rotatably locked but slidable connected to said housing, the medicament holder comprising first mix engagement means (28; 126) on its outer surface, and second linear guide means; a multi-chamber medicament container (14; 130) arranged within the container holder, a plunger rod (60; 140) comprising first holding means (58; 146) on its outer circumferential surface; drive force means (64; 142) capable of pushing said plunger rod; characterized in that said device further comprises manual mixing means (44, 148) comprising a rotatable manual knob (62,186) protruding from the distal end of the housing and a mix member (48; 149) comprising flexible holding means (52; 160) releasibly engaged to the first holding means (58; 146) for holding the plunger rod and thereby the drive force means in a pre-tensioned state and second mix engagement means (46; 150) arranged to cooperate with the first mix engagement means (28; 126) for linearly and distally displacing said container holder into the housing when said manual knob is rotated, such that the distal displacement of the container holder causes a distal displacement of the container in relation to the plunger rod, whereby the plunger rod forces the distal stopper to be proximally displaced and thereby a mixing of the components is performed.

13 Claims, 15 Drawing Sheets

(51) Int. Cl.
*A61M 5/20* (2006.01)
*A61M 5/24* (2006.01)
*A61M 5/32* (2006.01)

(52) U.S. Cl.
CPC ....... *A61M 5/326* (2013.01); *A61M 2005/2013* (2013.01); *A61M 2005/206* (2013.01); *A61M 2005/2073* (2013.01); *A61M 2005/2451* (2013.01); *A61M 2210/0618* (2013.01)
USPC ............................................ 604/89; 604/131

(56) References Cited

U.S. PATENT DOCUMENTS

| | | | |
|---|---|---|---|
| 8,403,883 B2 * | 3/2013 | Fayyaz et al. | 604/90 |
| 2003/0105430 A1 * | 6/2003 | Lavi et al. | 604/136 |
| 2009/0105637 A1 * | 4/2009 | Wang et al. | 604/89 |
| 2009/0259181 A1 | 10/2009 | Moser | |

* cited by examiner

MEDICAMENT DELIVERY DEVICE WITH MIXING MECHANISM

TECHNICAL AREA

The present invention relates to a medicament delivery device and in particular a medicament delivery device capable of handling multi-chamber medicament containers.

TECHNICAL BACKGROUND

It is becoming more and more common to use multi-chamber medicament containers in medicament delivery devices such as injectors. The reason for this is that the medicament can be stored for much longer time periods without being degraded in comparison with medicament dissolved in some liquid.

Thus the medicament and the liquid are kept in different compartments in the medicament container and are mixed just before use by moving a dividing wall or stopper such that the compartments can communicate with each other.

However, the multi-chamber medicament containers entail more handling steps before a dose of medicament can be injected in that the plunger rod of the injector has to move the stopper of the medicament container in order to initiate the mixing.

A number of solutions have been proposed for obtaining the mixing, from manual operation such as bringing together two parts of the injector to an automatic operation. The first is described in EP 0 288 443 in which a front cover of the injector is rotated whereby a medicament powder chamber is pushed against a plunger, which in turn breaks an aluminium membrane such that liquid is mixed with the powder.

An example of an automatic mixing function is disclosed in WO 2006/080893 wherein the spring actuated plunger rod can be pushed automatically a certain first distance, after which it is stopped. The plunger rod can then be released again and travel a certain second distance. During the first distance the mixing is performed and during the second distance the injection is performed.

Some users/patients prefer to attach a delivery member as a needle to the multi-chamber container before the mixing is performed, when the medicament is of such a kind that allows it. Also some multi-chamber containers may be syringes with an already inbuilt needle.

BRIEF DESCRIPTION OF THE INVENTION

The aim of the present invention is to provide a medicament delivery device that utilizes multi-chamber that is user-friendly and safe when handled.

This aim is obtained by the present invention defined by the features of the independent patent claim. Preferable embodiments of the invention form the subject of the dependent patent claims.

According to a major aspect of the invention, it is characterised by a medicament delivery device comprising a generally elongated housing having opposite distal and proximal ends; a medicament container holder rotatably locked but slidable connected to said housing, the medicament holder comprising first mix engagement means on its outer surface, and second linear guide means; a multi-chamber medicament container comprising at least two substances, and arranged within the container holder; a plunger rod comprising a proximal end arranged to act on a distal stopper arranged inside said container, and first holding means on its outer circumferential surface; drive force means extending along a longitudinal axis of the plunger rod and being in contact with the plunger rod, capable of pushing said plunger rod for acting on said distal stopper; wherein said device further comprises manual mixing means comprising a rotatable manual knob protruding from the distal end of the housing and a mix member comprising flexible holding means releasibly engaged to the first holding means for holding the plunger rod and thereby the drive force means in a pre-tensioned state and second mix engagement means arranged to cooperate with the first mix engagement means for linearly and distally displacing said container holder into the housing when said manual knob is rotated, such that the distal displacement of the container holder causes a distal displacement of the container in relation to the plunger rod, whereby the plunger rod forces the distal stopper to be proximally displaced and thereby a mixing of the components is performed.

According to a first embodiment of the invention, said device further comprises a medicament delivery activation member slidably arranged in said housing and surrounding said container holder, the activation member having a proximal part with a contact part intended to be applied against a delivery site and protruding from the proximal end of the housing, and second holding means releasibly engaged to the flexible holding means when the plunger rod and the holding means are in the pre-tensioned state.

According to other aspects of the first embodiment invention, said activation member comprises locking means arranged to be in contact with the proximal end of the mix member for preventing a distal movement of said medicament delivery activation member until said manual mixing has been performed; and said container holder comprises release means arranged to come in contact with the locking means when said container holder has been distally displaced for releasing said locking means and allowing the distal displacement of the activation member.

According to a further aspect of the first embodiment of the invention, said device further comprises an activation member force drive means arranged between the second holding means and a distal wall of the rotatable manual knob, wherein said activation member force drive means is capable of pushing said medicament delivery activation member to an extended state after withdrawing said activation member from the delivery site and wherein said locking means is capable of locking said activation member in said extended state when said locking means passes over said release means.

According to a second embodiment of the invention, said rotatable manual knob comprises second holding means releasibly engaged to the flexible holding means when the plunger rod and the holding means are in the pre-tensioned state; said device further comprises a medicament delivery activation means arranged to said container holder and radially protruding through elongated slits on the housing, such that when said activation means and thereby said container holder are proximally displaced, said flexible holding means are disengaged from both second holding means and said first holding means.

According to other aspects of the second embodiment invention said housing comprises first locking means arranged to be in contact with the proximal end of the mix member for preventing a proximal movement of said medicament delivery activation means until said manual mixing has been performed; and said container holder comprises release means arranged to come in contact with the first locking means when said container holder has been distally displaced for releasing said first locking means and allowing a proximal displacement of the activation means.

According to a further aspects of the second embodiment of the invention, said device further comprises a retraction force drive means arranged between a first annular ledge of the mix member and a second annular ledge of the housing, wherein said retraction force drive means is compressed when said activation means are proximally displaced; and said mix member further comprises second locking means arranged to come in contact with corresponding third locking means of a locking sleeve which is rotationally locked to both the rotatable manual knob and the mix member, for locking said activation means in a retracted position within the housing when said activation means are released after a medicament delivery and the compressed retraction force drive means forces the mix member to be distally displaced.

There are several advantages with the present invention. The manual mixing provides a simple, and yet reliable mixing operation with few components. At the same time, since the delivery operation is performed automatically by activation by pushing the medicament delivery activation member, it is important that the medicament delivery activation member is locked until the mixing has been performed properly.

Preferably the user has to perform a further step in order to release the medicament delivery activation member and at the same time priming the container, such as turning the mixing knob a further step after the mixing operation. Also preferably, the turning of the mixing knob causes the locking means to release the medicament delivery member shield. Thereby an efficient function of the components of the device is obtained.

Further, in order to ascertain that the device cannot cause unintentional needle sticks after use, the medicament delivery activation member is locked in an extended state after the device has been removed from the delivery site.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
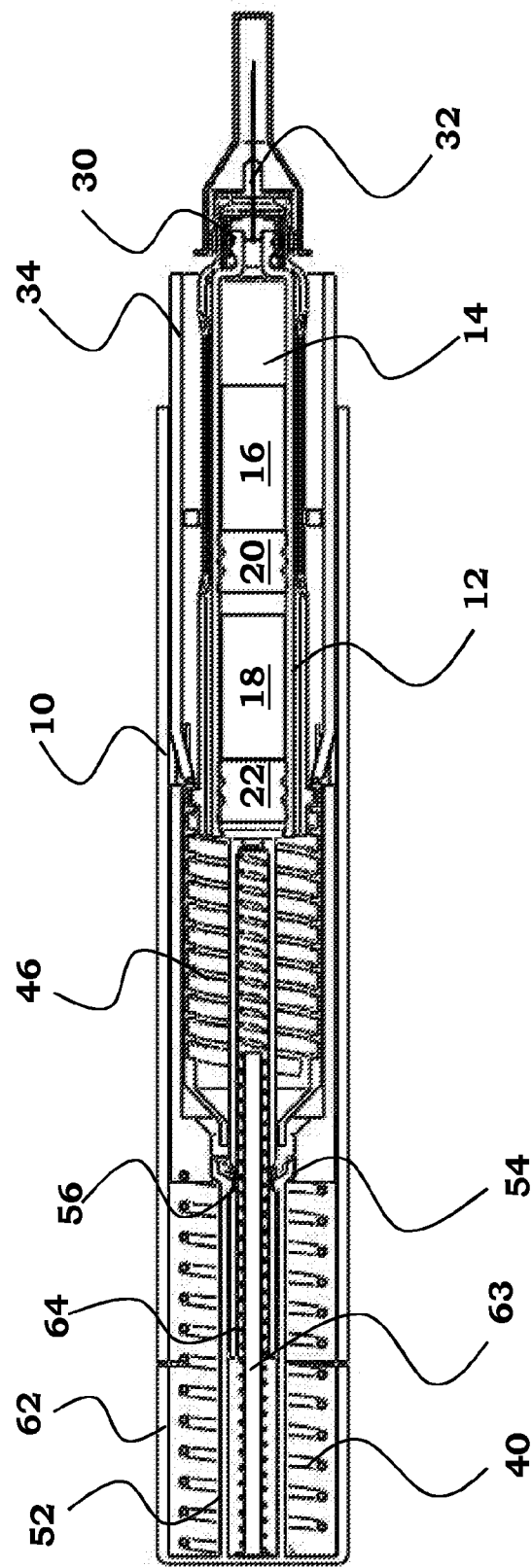
FIG. 1 is a cross-sectional view of a first embodiment of a medicament delivery device according to the present invention.
Figure 2:
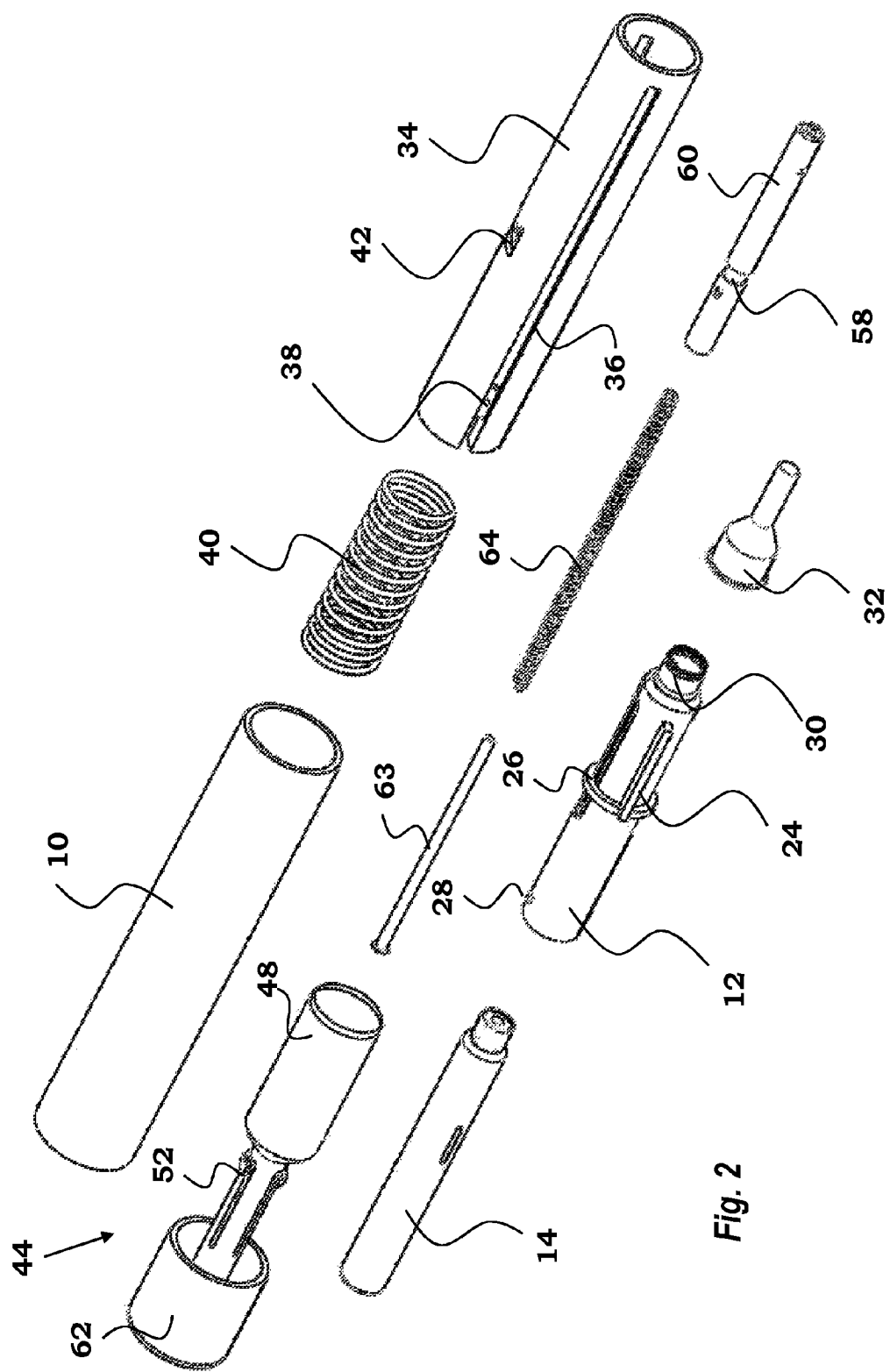
FIG. 2 is an exploded view of the medicament delivery device of FIG. 1, FIGS. 3-7 are cross-sectional views of the embodiment of FIG. 1 in different functional positions.
Figure 3:
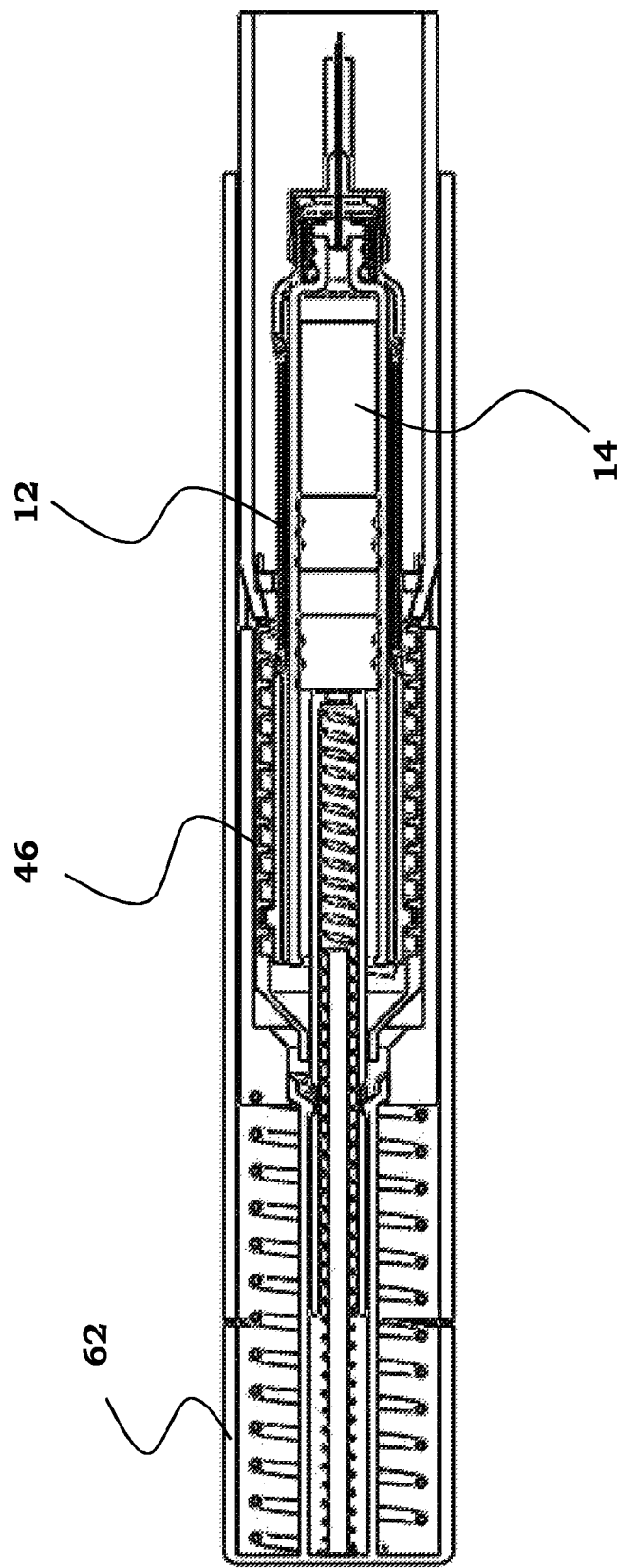

In the present application, when the term "distal part/end" is used, this refers to the part/end of the delivery device, or the parts/ends of the members thereof, which is/are located the furthest away from the medicament delivery site. Correspondingly, when the term "proximal part/end" is used, this refers to the part/end of the delivery device, or the parts/ends of the members thereof, which, is/are located closest to the medicament delivery site.

The medicament delivery device e.g. an auto-injector as shown in the FIGS. 1-7 comprises a generally tubular elongated housing 10 having opposite distal and proximal ends. In the proximal end of the medicament delivery device, a medicament container holder 12 is arranged. Inside the medicament container holder a multi-chamber medicament container 14 is arranged, in the shown case two chambers 16, 18 separated by a stopper 20. A further distal stopper 22 is arranged at the distal end of the container. The outer surface of the container holder is arranged with longitudinally extending ledges 24; release means 26 as an annular ledge; first engagement means 28 as two outwardly directed and diametrically arranged protrusions, the function of which will be explained below; and proximal attachment means 30 arranged to cooperate with corresponding attachment means of a delivery member 32. The medicament delivery member can be a mouth or nasal piece, which the patient puts in his mouth or nose. The medicament delivery member can be a member that introduces the medicament to the eye of the patient, such as a suitable nozzle that sprays the medicament to the eye, or a member that introduces the medicament to the eye in the form of droplets. Naturally, a nozzle as a medicament delivery member can also be used in order to spray the medicament onto the skin of the patient. The medicament delivery member can also be a needle for the injection of the medicament into the body of the patient.

The inner surface of the housing is arranged with longitudinally extending ledges at its proximal end. The longitudinal ledges 24 of the container holder and the longitudinal ledges of the housing cooperate with corresponding slits 36 on the surface of a medicament delivery activation member 34, preventing rotation of the container holder but allowing axial movement.

A plunger rod 60 arranged within said housing comprises a proximal end abutting on the distal stopper 22 and first holding means 58 as an annular groove on its outer circumferential surface.

A drive force means 64 is arranged extending along a longitudinal axis of the plunger rod and being in contact with the plunger rod. In the embodiment shown in the FIGS. 1-8, the plunger rod is a hollow plunger rod and the drive force means is a spiral spring arranged within said plunger rod. Moreover, a guide spike 63 for the spring is arranged inside the spring.

The container holder is surrounded by the generally tubular medicament delivery activation member 34 slidably arranged in said housing. The activation member comprises a proximal part with a contact part intended to be applied against a delivery site and wherein said proximal part protrudes somewhat from the proximal end of the housing. The activation member also comprises second holding means 38 arranged as an inwardly directed annular ledge on its inner circumferential surface, the function of which will be described below.

The device further comprises manual mixing means 44 comprising a rotatable manual knob 62 protruding from the distal end of the housing and a mix member 48 comprising flexible holding means 52 and second mix engagement means 46. The flexible holding means being a number of flexible tongues on the circumference of the mix member. Each flexible tongue comprising an outwardly extending protrusion 54 and inwardly extending ledge 56, wherein each inwardly extending ledge 56 fits into the annular groove 58 of the plunger rod 60 that is partially and slidable arranged inside said mix member for holding the plunger rod and thereby the drive force means in a pre-tensioned state. The inwardly directed annular ledge 38 is in contact with the outwardly extending protrusions 54 of the flexible tongues 52, thereby preventing the medicament delivery activation member to be proximally displaced and holding the inwardly extending ledges 56 engaged to the annular groove 58 of the plunger rod 60. The second mix engagement means 46 being e.g. threads on the inner circumferential surface of the mix member, are arranged to cooperate with the first mix engagement means 28 for distally displacing said container holder into the housing when said manual knob is rotated, such that the distal displacement of the container holder causes a distal displacement of the container in relation to the plunger rod, whereby the plunger rod forces the distal stopper to be proximally displaced and thereby a mixing of the components is performed.

Further an activation member force drive means 40 as a spring, hereafter named medicament delivery activation member spring, is arranged between the inwardly directed annular ledge 38 of the activation member and an inner surface of a distal wall of the rotatable manual knob 62. Since the inwardly directed annular ledge 38 is in contact with the outwardly extending protrusions 54 of the flexible tongues 52, the medicament delivery activation member is prevented of being proximally displaced due to the force of the spring 40.

Further, locking means 42 are arranged as flexible tongues on the medicament delivery activation member 34 wherein said tongues 42 are arranged to be in contact with the proximal end of the mix member for preventing a distal movement of said medicament delivery activation member until said manual mixing has been performed.

The device is intended to function as follows. FIG. 1 shows the device when it is delivered to the patient. When the device is delivered to a user, the multi-chamber medicament container is preferably already positioned in the device. In order to perform a medicament delivery a mixing has to be performed first. When the container is a cartridge, the user first attaches a medicament delivery member, such as an injection needle 32 onto the neck 30 of the container holder 12. When the container is a syringe, the delivery member is already mounted on the container. In order to perform the mixing operation the rotatable manual knob 62 is rotated relative the housing. Because the rotatable manual knob 62 is fixedly attached to the mix member 48, it will also rotate, whereby the protrusions 28 of the container holder 12 will ride in the threads 46. This in its turn causes the container holder 12 to be distally displaced into the housing 10 and against the plunger rod 60, whereby a protective needle cap of the needle is pushed off when the needle cap comes into contact against the annular surface at the proximal end of the medicament delivery activation member. Rotation of the container holder 12 is prevented by the longitudinal ledges 24. This relative movement of the container holder 12 and thus medicament container 14 in relation to the plunger rod 60 causes the distal stopper 22 to move such that passages are obtained between the chambers 16, 18 of the medicament container and thus a mixing of the medicament in powder form with a diluent is obtained, FIG. 3.

Figure 4:
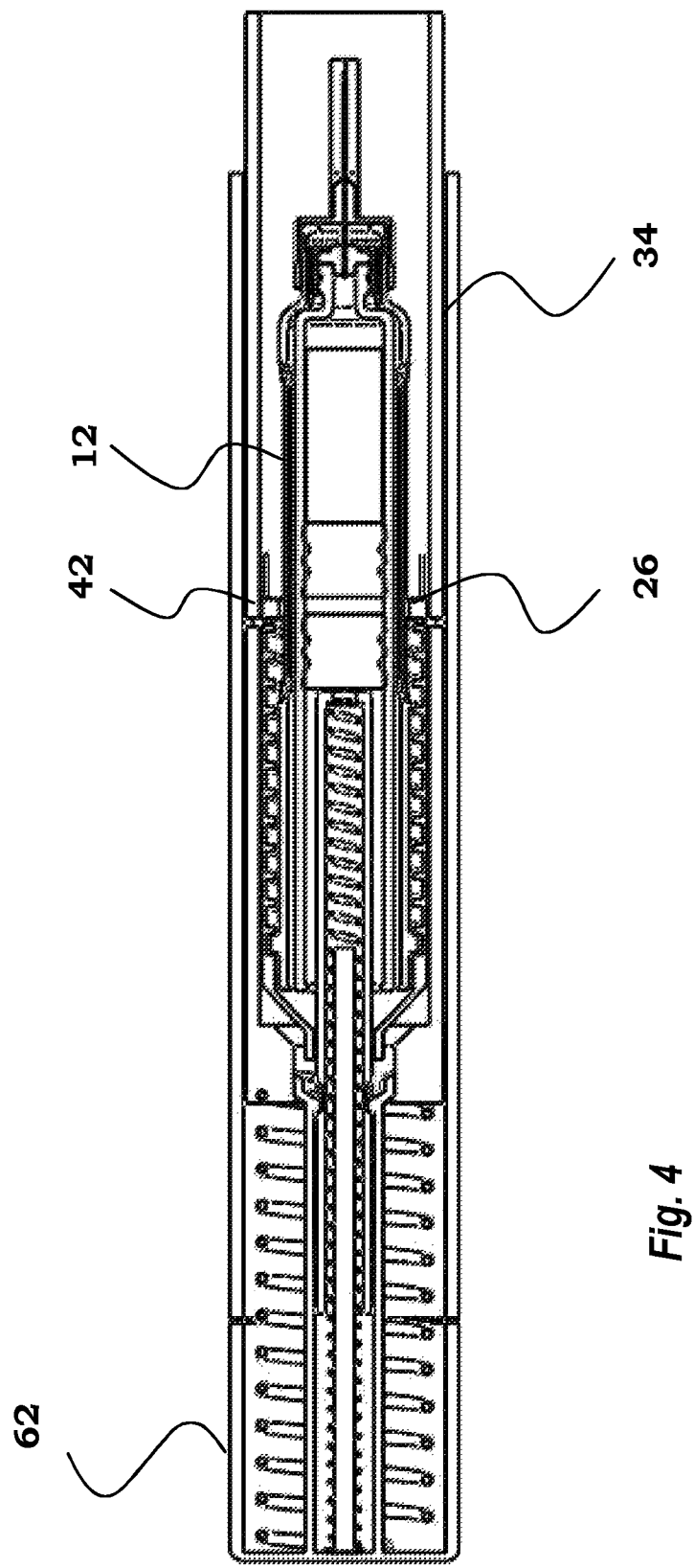
Figure 5:
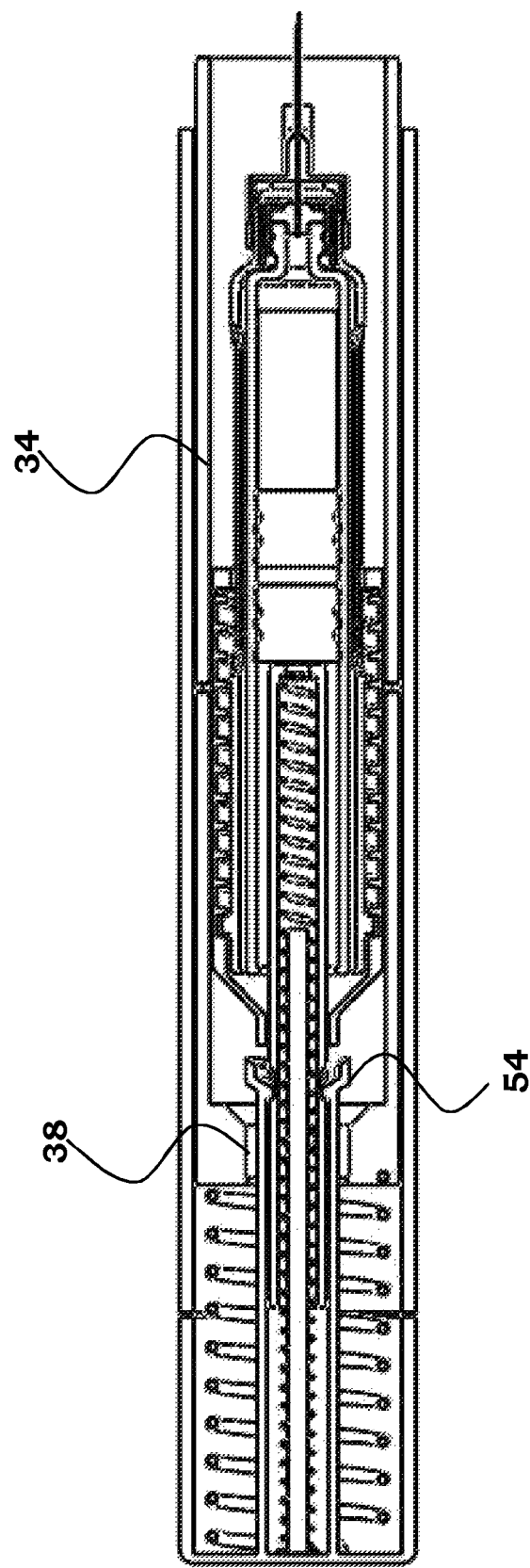
Figure 6:
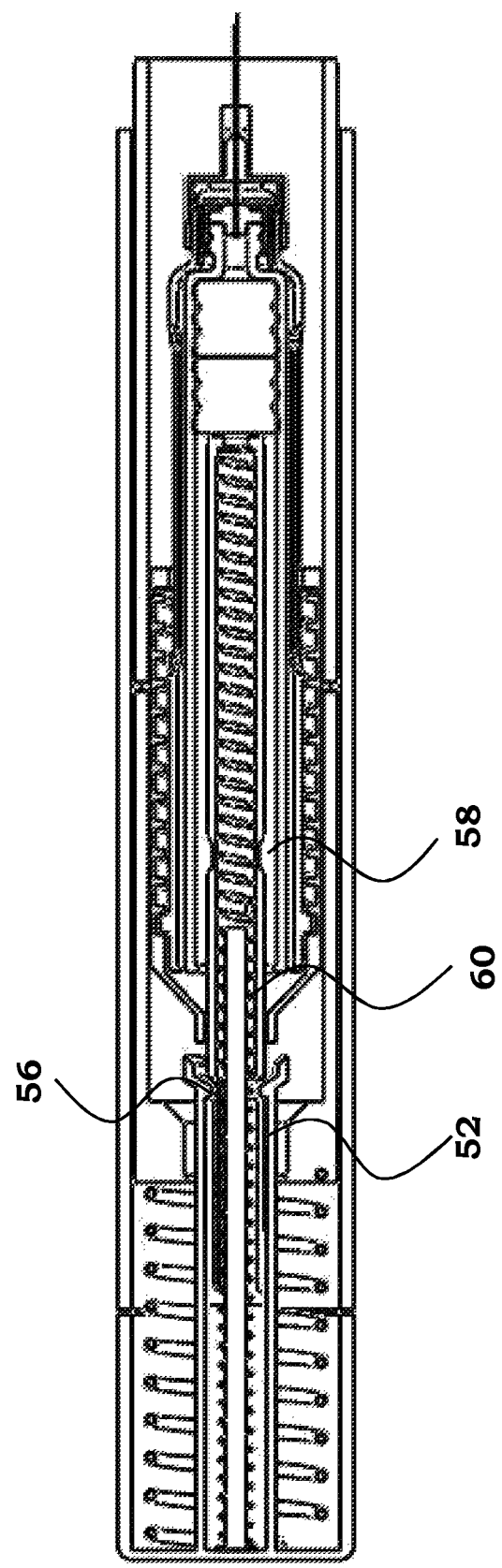
Figure 7:
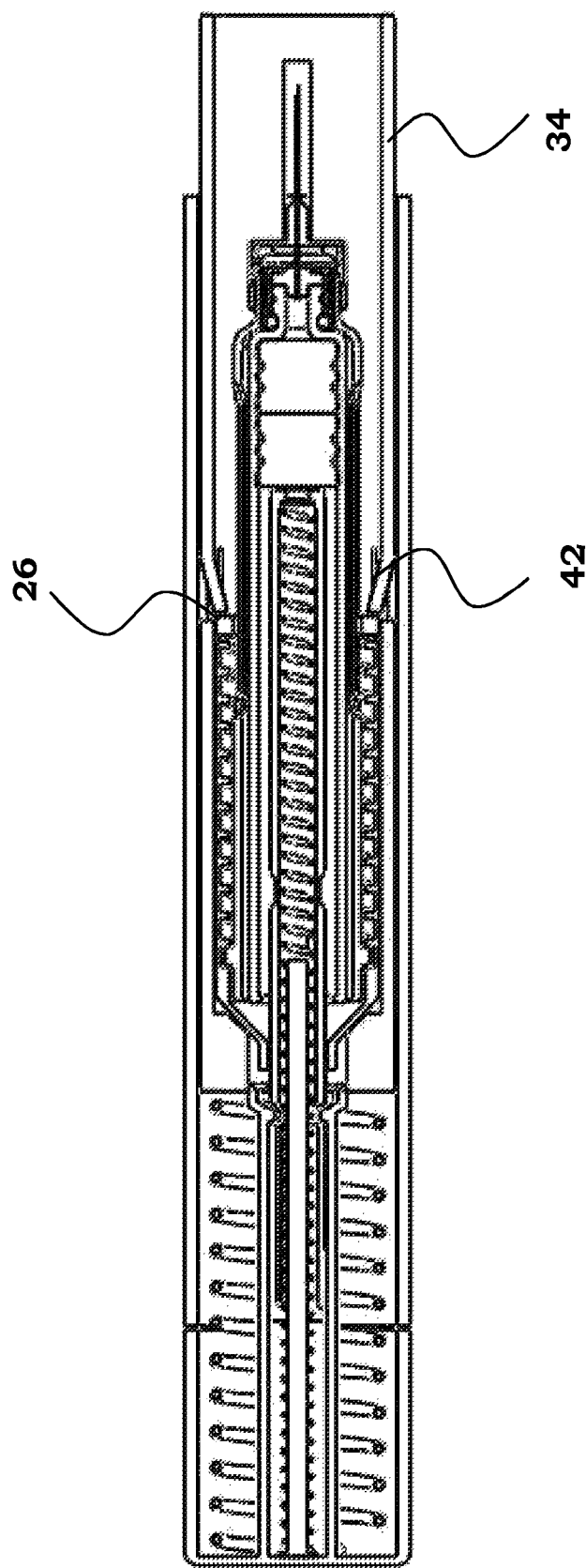
Figure 8A:
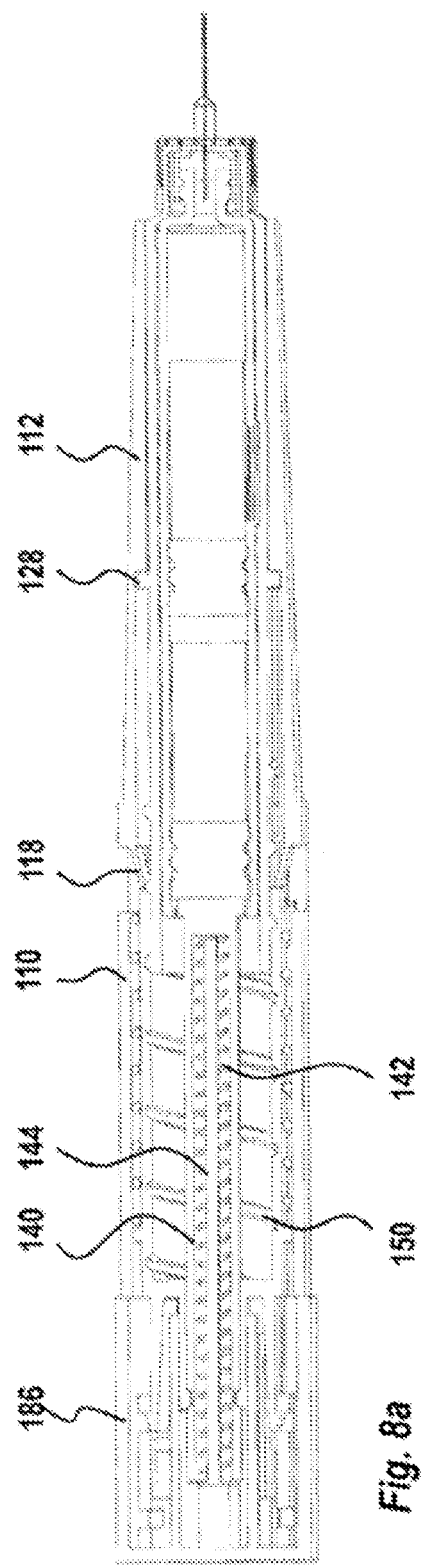
FIG. 8a is a cross-sectional view of an alternative embodiment of a medicament delivery device according to the present invention.
Figure 8B:
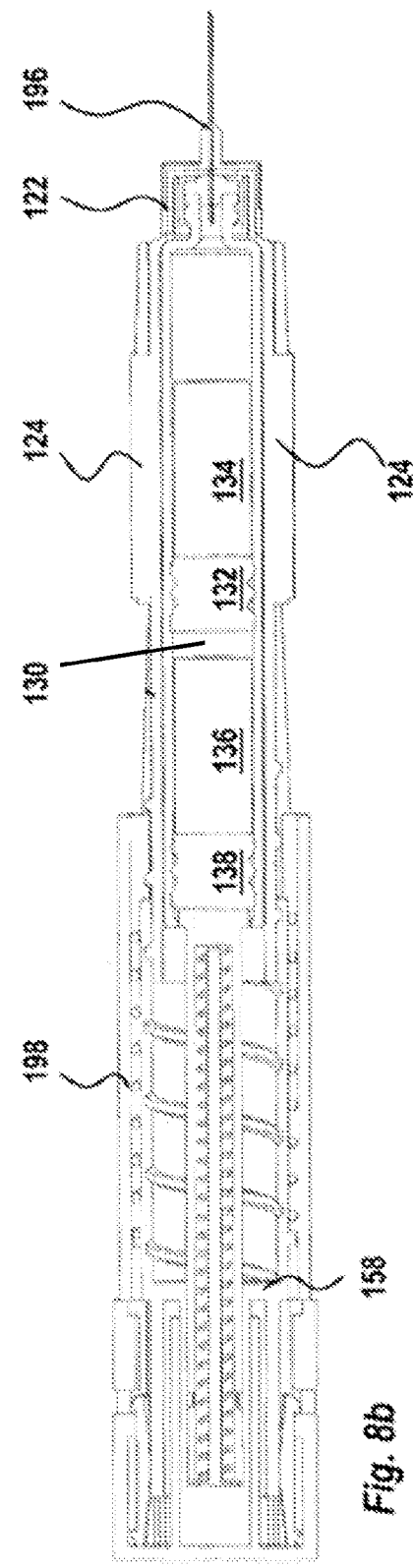
FIG. 8b is a cross-sectional view of the device of FIG. 1 turned 90°.
Figure 9:
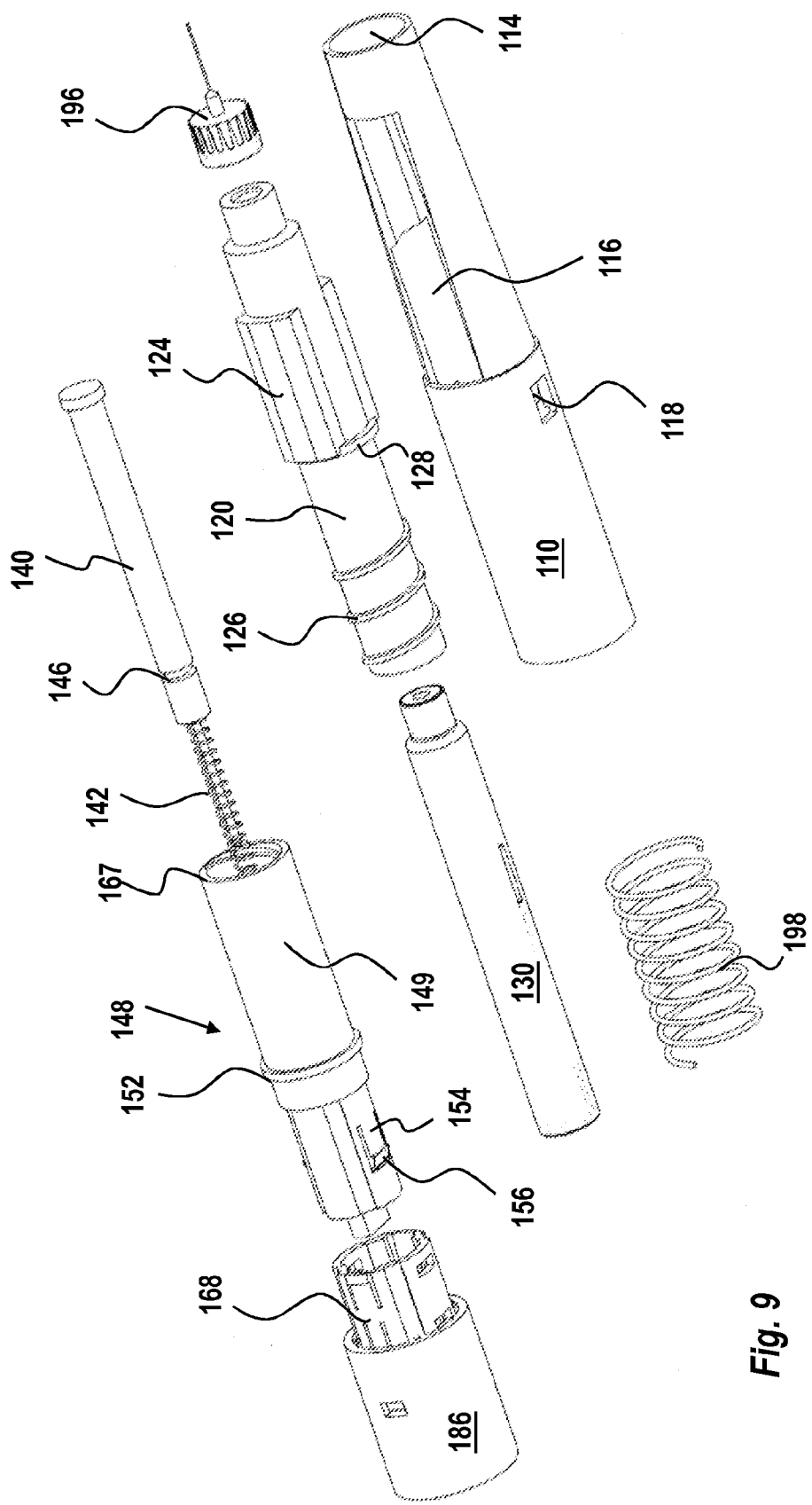
FIG. 9 is an exploded view of the medicament delivery device of FIG. 8.
Figure 10:
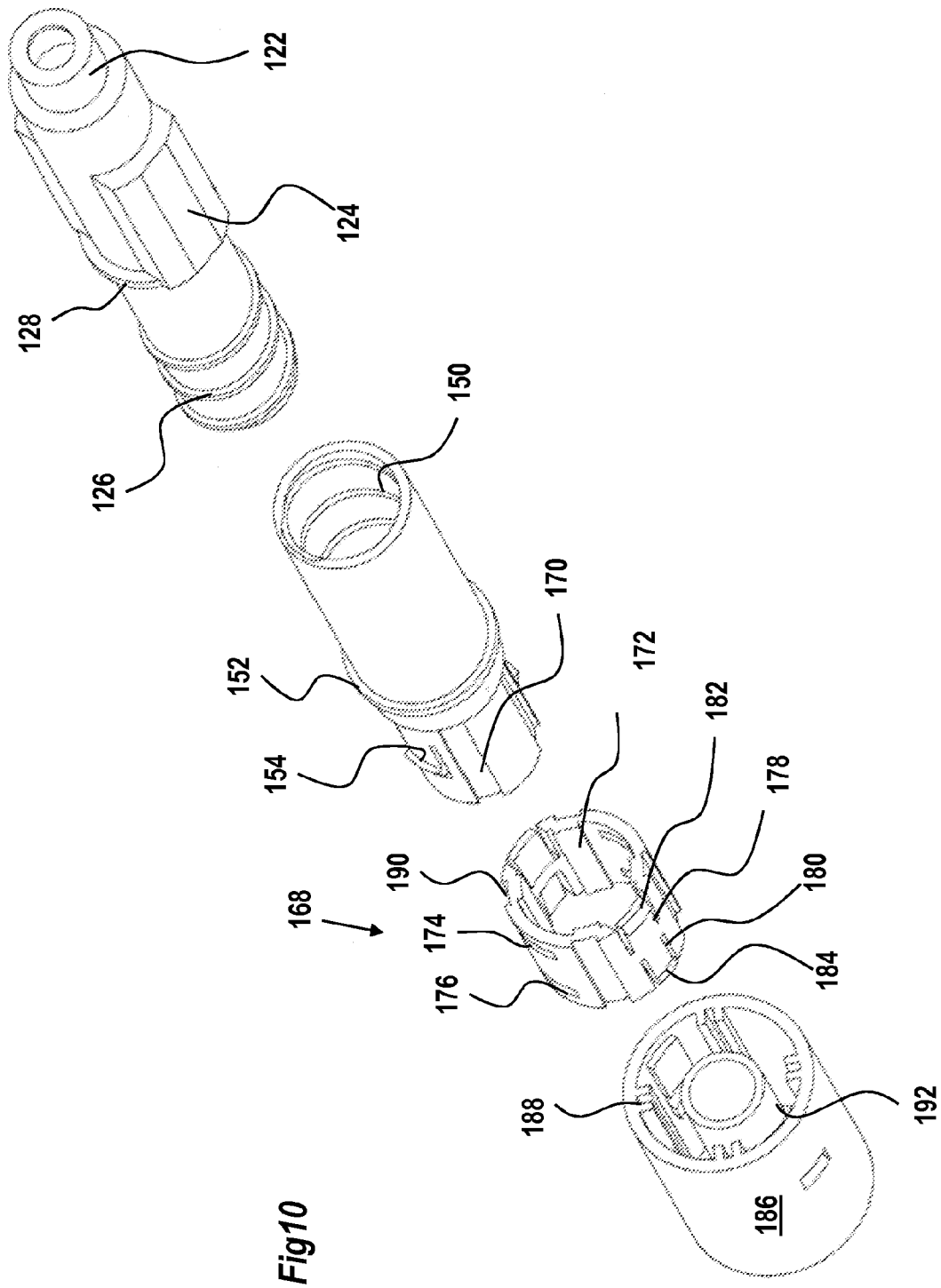
FIG. 10 is a detailed view of a mixing and locking mechanism comprised in the present invention.
Figure 11:
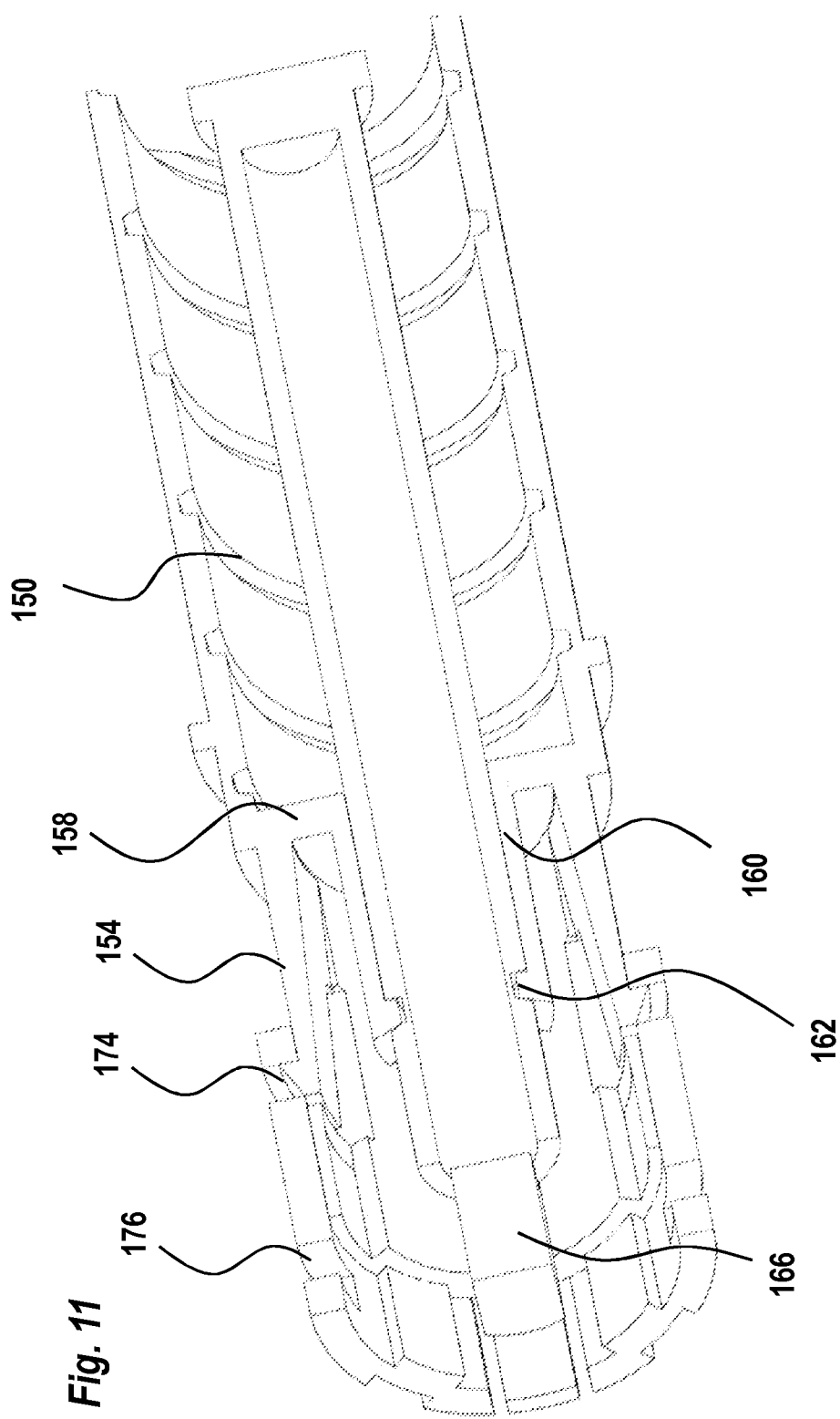
FIG. 11 is a detailed view in cross-section of a mechanism for locking a plunger rod comprised in the present invention.
Figure 12:
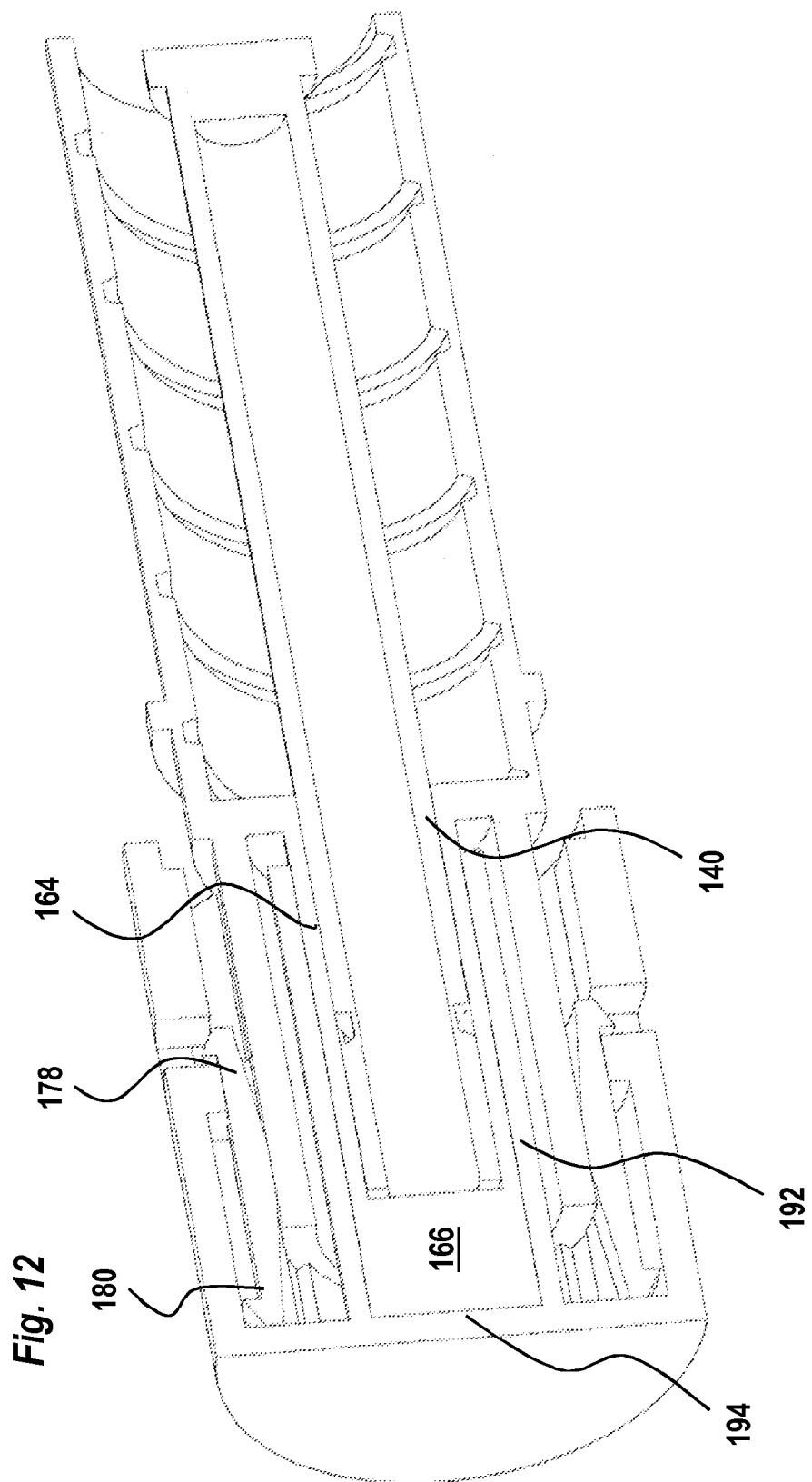
FIG. 12 is detailed view according to FIG. 11 turned 90°.
Figure 13A:
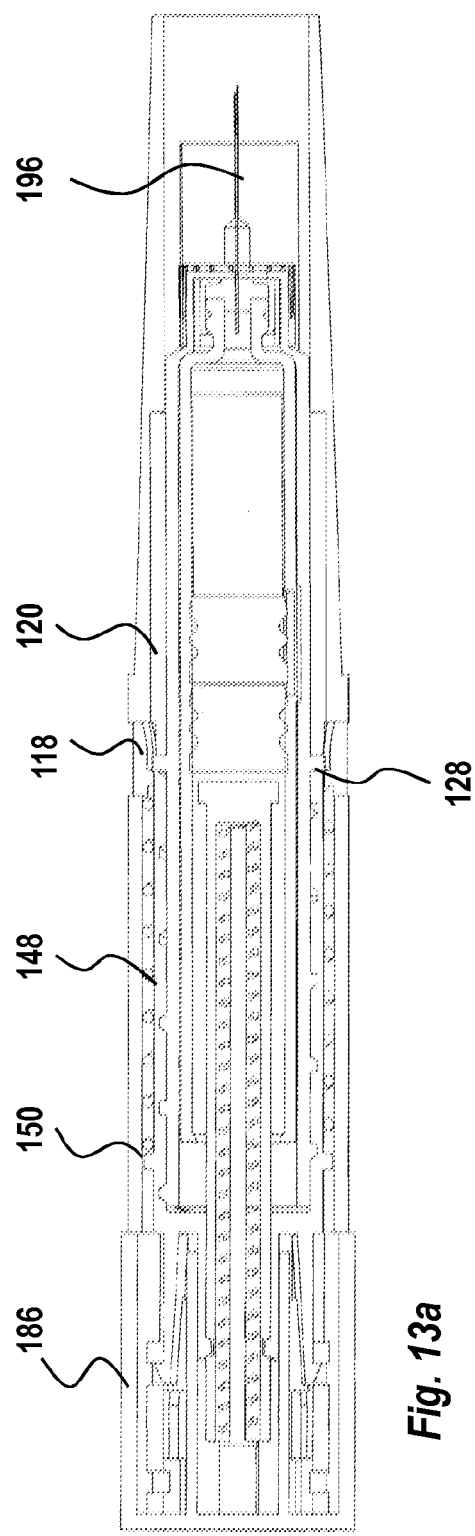
FIGS. 13-15 are cross-sectional side views of different functional stages of a device according to the present invention.
Figure 13B:
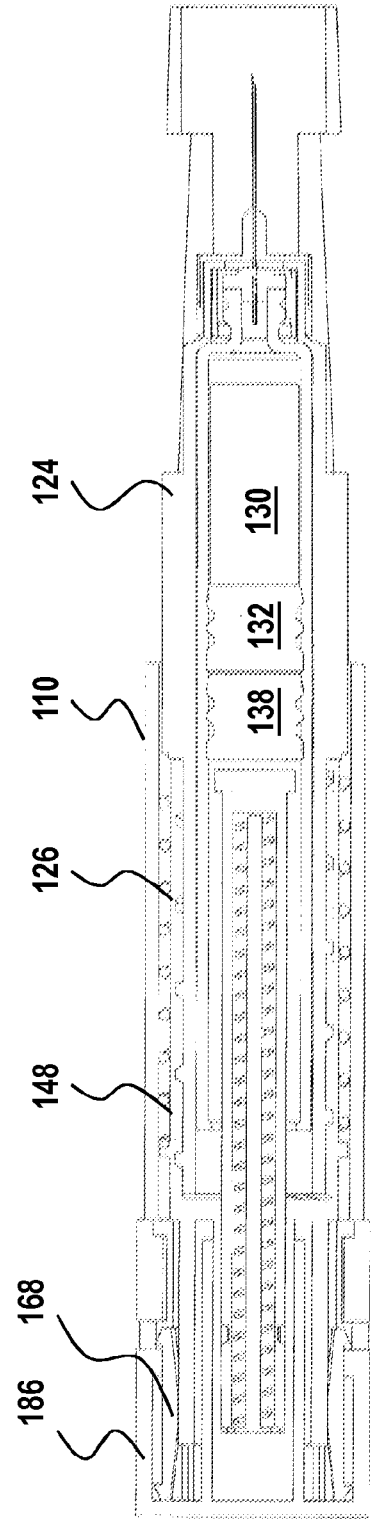
Figure 14A:
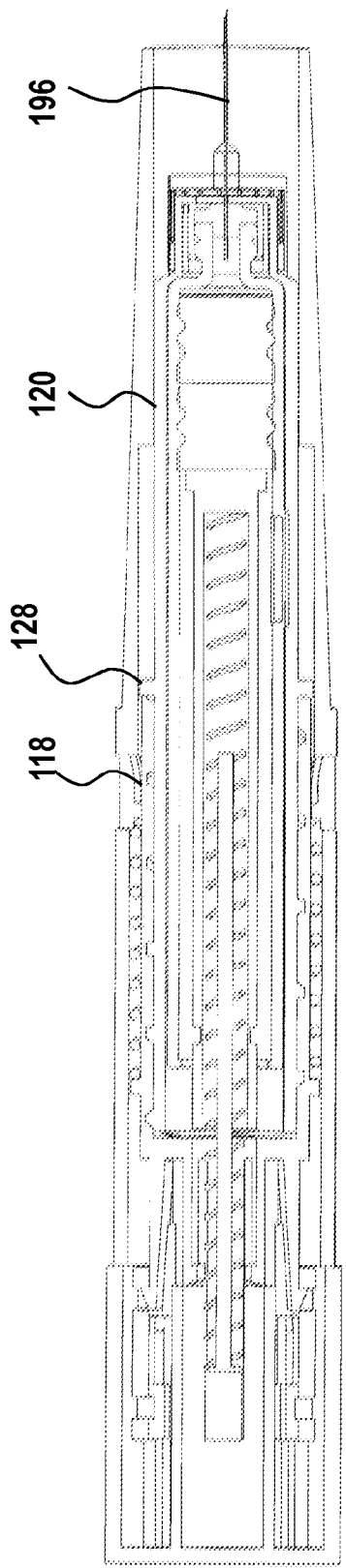
Figure 14B:
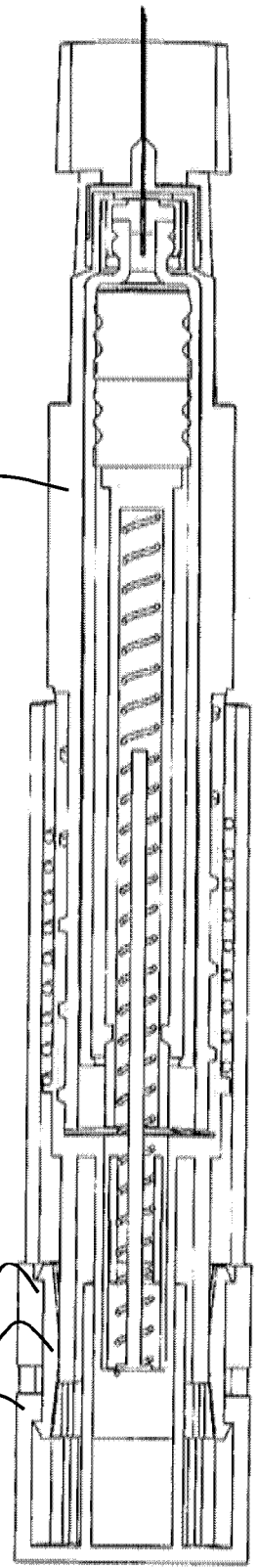
Figures 15A, 15B:
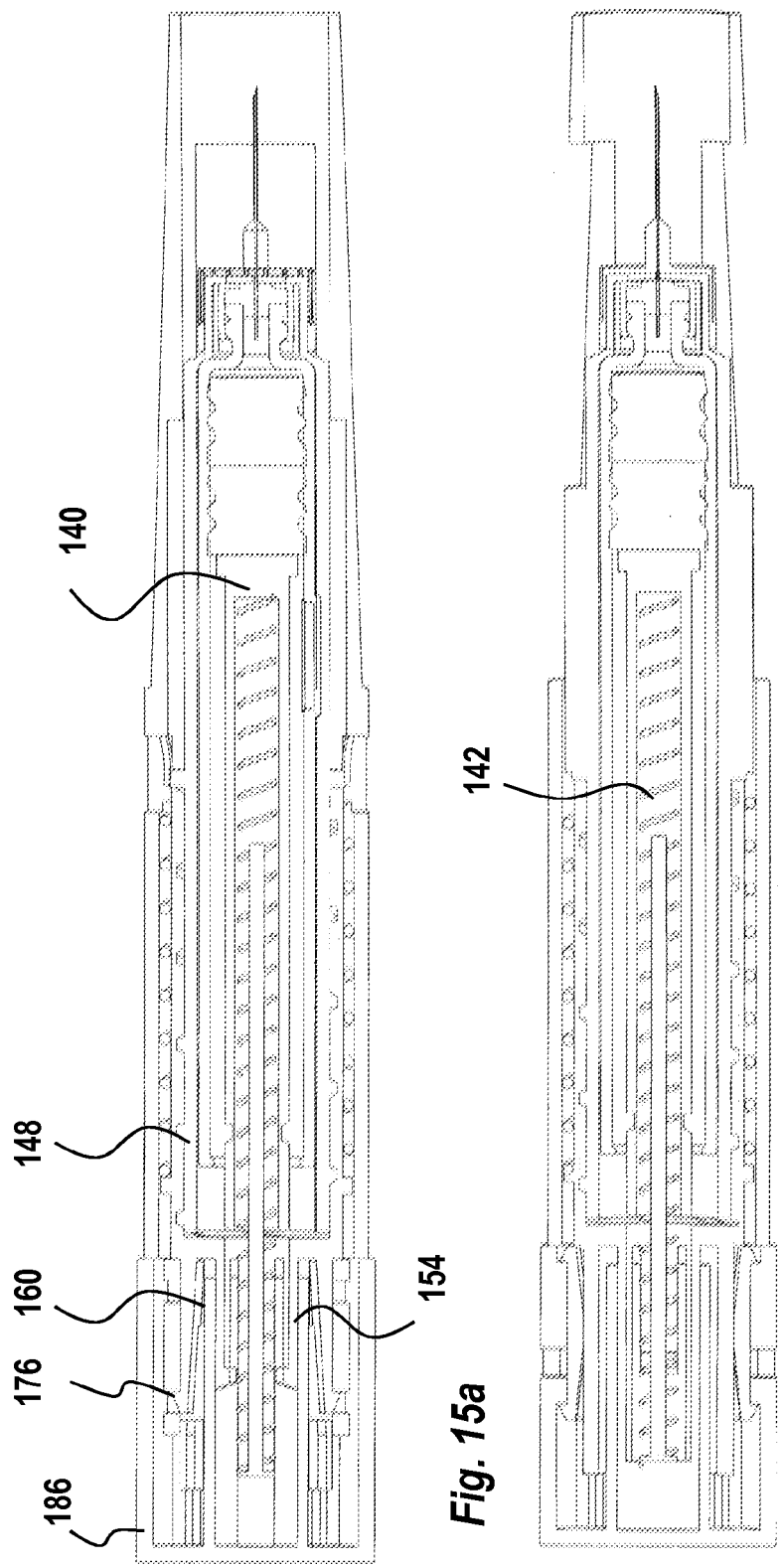

The knob 62 is now turned somewhat further, whereby the container holder 12 is somewhat distally displaced such that the annular ledge 26 of the container holder comes in contact with the locking members 42 of the medicament delivery activation member 34 such that they are forced radially outwards and out of contact with the annular surface of the mix member 48, FIG. 4. This further movement is also achieved for priming, since this relative movement of the container holder 12 and thus the medicament container 14 in relation to the plunger rod 60 causes the stoppers 22 and 20 to move somewhat inside. The medicament delivery activation member 34 is now free to be distally displaced and the device is ready for the delivery step.

The proximal end of the activation member is pressed against the delivery site whereby the medicament delivery activation member 34 is pushed inside the housing, wherein the penetration of the needle into the delivery site is performed. When the medicament delivery activation member has moved distally a certain distance, the inwardly directed annular ledge 38 has been moved out of contact with the outwardly extending protrusions 54 of the flexible tongues 52 of the mix member 48, FIG. 5. The flexible tongues 52 are thus free to flex radially outwards whereby the inwardly directed ledges 56 of the flexible tongues are moved out of contact with the annular groove 58 of the plunger rod 60.

The plunger rod 60 is in turn free to move and is pushed proximally by the spring 64. The proximal movement of the plunger rod causes the stoppers 20, 22 inside the container 14 to move proximally, whereby a dose of medicament is injected through the needle. When the stoppers have reached the foremost position of the container, the delivery is completed and the device can be withdrawn from the delivery site, FIG. 6. The medicament delivery activation member 34 will thereby move proximally and cover the needle due to the action of the spring 40. The outwardly extending protrusions 54 of the flexible tongues 52 can now no longer stop or hold the medicament delivery activation member 34 because the flexible tongues 52 have passed the plunger rod so that when the annular ledge 38 comes in contact with the protrusions of the flexible tongues 52, the flexible tongues 52 will flex inwards and the medicament delivery activation member will pass proximally. The medicament delivery activation member is then locked from being pushed inside due to that the locking members 42 of the medicament delivery activation member have passed over the annular ledge 26 of the container holder, FIG. 7.

It is also possible that medicament delivery activation member is a slidable side button (not shown) having an annular ledge (not shown) in contact with the outwardly extending protrusions 54 of the flexible tongues 52, a protruding part (not shown) through the side surface of the housing 10, and locking means as a removable cover (not shown) for preventing premature activation.

FIGS. 8-15 show a variant of the present invention. It comprises a generally tubular elongated housing 110 having a proximal part 112 with a somewhat smaller diameter and conical in the proximal direction. The proximal end of the housing 110 is provided with a central opening 114. Further the proximal part of the housing is arranged with two oppositely positioned slits 116 that extend in the elongated direction. The housing is also arranged with first locking means 118 as two tabs extending in the distal direction at an angle inwards in relation to the longitudinal direction.

Inside the housing a container holder 120 is arranged, also having a generally tubular shape and provided with a proximal attachment means 122 onto a neck portion, such as threads, onto which a medicament delivery member having corresponding attachment means, may be attached, such as an injection needle as shown. It is however to be understood that other types of attachment members, such as bayonet fittings, snap-on members and the like may be employed. It is also to be understood that other types of medicament delivery members may be used such as mouth pieces, nozzles, and the like can be used.

The container holder is further arranged with medicament delivery activation means 124 such as two outwardly projecting ledges on the side surface, where the ledges are positioned opposite each other and dimensioned and positioned such that they fit into the slits 116 of the housing. Further the container holder is arranged with first mix engagement means 126 such as threads on its outer distal surface and with release means 128 such as radial outwardly extending ledges.

Inside the container holder a medicament container 130 can be positioned, having a proximal neck portion arranged to fit into the neck portion of the container holder. The container according to the present invention may be a multi-chamber container, in most instances a dual-chamber container, having a first stopper 132 dividing two compartments 134, 136, one with medicament and one with diluent, as well as a distal stopper 138 closing the distal end of the medicament container 130.

A plunger rod 140 is further arranged inside the device in the form of a generally tubular member extending in the longitudinal direction of the device. The proximal end of the plunger rod is arranged to be in contact with the distal stopper 138 of the medicament container 130. Inside the plunger rod a drive force means 142 is arranged, in the embodiment shown a compression spring. The spring 142 is further arranged with a guide pin 144 inside the spring. The plunger rod is further arranged with first holding means 146 such as a circumferential groove on its distal circumferential outer surface.

Surrounding the plunger rod is a manual mixing means 148 comprising a rotatable manual knob 186 protruding from the distal end of the housing and a mix member 149. The mix member is arranged with second mix engagement means 150 such as threads, on its inner proximal circumferential surface, which threads are intended to cooperate with the threads 126 of the container holder 120 in a manner that will be described below. Further the mix member is provided with a circumferential first annular ledge 152, intended to cooperate with the first locking means 118 i.e. the tabs of the housing in a manner that will be described below. The distal end of the mix member is arranged with two U-shaped slits on opposite sides, each forming a second locking means 154 such as a flexible arm 154 extending in the distal direction of the device. The ends of the arms are arranged with outwardly extending ledges 156, each having a wedge-shape in the distal direction. The distal part of the mix member is further arranged with a transversal interior wall 158 provided with a passage. At the distal surface of the wall adjacent the passage, flexible holding means 160 such as two flexible arms are attached, extending in the distal direction. The end of each arm is provided with an inwardly directed ledge 162 arranged and adapted to fit into the circumferential groove 146 of the plunger rod 140. Further two posts 164 are also attached to the distal surface of the wall extending in the distal direction. The two posts are connected at their ends by a transversal post 166, which will act as an end surface for the plunger rod. In the initial position the tabs 118 of the housing are in contact with a proximal end annular surface 167 of the mix member 149.

A locking sleeve 168 is arranged surrounding the distal part of the mix member 149. The outer surface of the distal area of the mix member 149 and the inner surface of the locking sleeve 168 are arranged with elongated grooves 170 and corresponding elongated ledges 172 such that a rotational lock is obtained between the two, but allowing a linear movement between the two. Further the locking sleeve 168 is arranged with third locking means 174, 176 such as two pairs of transversal through-going slits positioned after each other in the longitudinal direction, which slits are arranged to cooperate with the outwardly directed ledges 156 of the arms 154 of the mix member 149. The locking sleeve 168 is also arranged with two sets of oppositely arranged flexible arms 178, 180, where one arm is in the proximal direction and the other arm is in the distal direction. Each arm is arranged with inwardly directed ledges 182, 184 having wedge-shaped form in the directions of the arms.

The locking sleeve is surrounded by the knob 186. The inner circumferential surface of the knob 186 is arranged with ledges 188 arranged to cooperate with corresponding grooves 190 of the locking sleeve 168 in order to obtain a rotational lock between the two but to allow axial movement between them. The inner circumferential surface of the mix member is further arranged with a ledge having a distal end surface and a proximal end surface which are to cooperate with the arms 180 of the locking sleeve 168 in a manner that will be described in detail below. Further the knob 186 is arranged with a second holding means 192 such as a centrally arranged tubular part attached to an end wall 194 of the knob 186, wherein the posts 164 and the transversal beam 166 of the mix member fits into said tubular part 192, forming a guide and an abutment surface.

The device is intended to function as follows. When the device is delivered to a user, a multi-chamber medicament container 130 is preferably already positioned in the device. In order to perform a medicament delivery a mixing has to be performed first. When the container is a cartridge, the user first attaches a medicament delivery member, such as an injection needle 196. When the container is a syringe, the delivery member is already mounted on the container. The user then turns the knob 186 at the distal end of the device with one hand while holding the housing 110 with the other hand. Because the knob 186 is rotationally locked to the locking sleeve 168, the locking sleeve will also rotate. Further since the locking sleeve 168 is rotationally locked to the mix member 149, the mix member is also rotated. The rotation of the mix member 149 causes the medicament container holder 120 to be moved in the distal direction due to the threaded connection between the mix member 149 and the medicament container holder 120, and also due to that the medicament container holder 120 is rotationally locked in relation to the housing 110 due to the ledges 124 protruding through the slits 116 of the housing. The medicament holder is thus drawn into the housing as well as the medicament delivery member whereby a protective cap of the delivery member is pushed off when the protective cap comes into contact against the annular surface at the proximal end of the housing. Due to the distal movement of the medicament container holder 120 and the medicament container 130, the distal stopper is pushed against the plunger rod 140 until the distal stopper is positioned such that passages are opened between the chambers 134, 136 of the medicament container, enabling a mixing of the medicament and the diluent, FIG. 13. The end of the mixing procedure also causes the medicament container to be primed, i.e. removing air entrapped inside the container. The delivery device is now ready for delivery. In the case of an injection device, the proximal end of the device is placed at the injection site. In order to perform a penetration, the user then grips the ledges 124 of the medicament container holder 120 protruding through the housing 110 with a pen grip and pushes the ledges/medicament container holder in the proximal direction whereby a penetration is performed. This action is now possible since the ledge 128 of the medicament container holder 120 has come in contact with the tabs 118 of the housing causing them to flex outwardly such that they are moved out of contact with the proximal end surface 167 of the mix member 149.

The proximal movement of the medicament container holder 120 causes the distally directed arms 160 holding the plunger rod 140 to move in the proximal direction in relation to the stationary knob 186 and thus in relation to the tubular part 192 such that the arms 160 are moved out of contact with the tubular part 192, and are therefore free to move outwards in the radial direction. The inwardly directed ledges 162 of the arms 160 are then moved out of contact with the circumferential groove 146 of the plunger rod 140, where the latter is free to move in the proximal direction due to the force of the compression spring 142. This proximal movement of the plunger rod 140 causes the stoppers 132, 138 to move in the proximal direction and to deliver a dose of medicament through the medicament delivery member, FIG. 14. The proximal movement of the mix member 149 also causes a proximal movement of the locking sleeve 168 due to the distally directed arms 154 of the mix member 149 being in engagement with the proximally arranged transversal slit 174 of the locking sleeve. At the same time the arms 180 engages the proximal and distal ledges 189, 191 on the inner surface of the mixing knob thereby locking the movement of the locking sleeve.

When the injection is performed the device can be removed from the delivery site. The user then lifts the device, still holding it with a pen-like grip. A retraction force drive means 198 such as a spring, arranged between the proximal side surface of the first annular ledge 152 of the mix member 149 and a distal side surface of a second annular ledge on the inner surface of the housing (not shown) causes the medicament holder 120 with the medicament container 130 and needle 196 as well as the mix member 149 to move in the distal direction in relation to the housing whereby the needle 196 is drawn into the housing, whereby it is protected against accidental needle sticks. At the same time the ledges of the flexible arms 154 of the mix member 149 fit into the grooves 176 of the locking sleeve, whereby also the mix member is locked against linear movement and thus also the medicament container holder, the medicament container and the injection needle, FIG. 15.

It is also possible that the device described in FIGS. 8-15 is arranged with a pre-tensed penetration spring (not shown) arranged between the distal annular ledge of the locking sleeve (168) and the inner surface of the distal wall 194, wherein said penetration spring is held in a pre-tensed state by the a locking-activation means (not shown) arranged between the side surface of the knob 186 and the flexible arms 178. It is also to be understood the locking-activation means are locked by a suitable manner such as a removable cover for avoiding premature activation of the delivery.

It is to be understood that the embodiment described above and shown in the drawings is to be regarded only as a non-limiting example of the invention and that it may be modified in many ways within the scope of the present invention.

The invention claimed is:

1. A medicament delivery device, comprising:
a generally elongated housing having opposite distal and proximal ends;
a medicament container holder rotatably locked but slidably connected to the housing, the medicament holder having a first mix engagement mechanism on its outer surface and a second linear guide mechanism;
a multi-chamber medicament container having at least two substances arranged within the container holder;
a plunger rod having a proximal end arranged to act on a distal stopper arranged inside the container, and a first holding mechanism on its outer circumferential surface;
a drive force mechanism extending along a longitudinal axis of the plunger rod and being in contact with the plunger rod, configured for pushing the plunger rod for acting on the distal stopper; and
a manual mixing mechanism having a rotatable manual knob protruding from the distal end of the housing, and a mix member having a flexible holding mechanism releasably engaged to the first holding mechanism for holding the plunger rod and thereby the drive force mechanism in a pre-tensioned state, and a second mix engagement mechanism arranged to cooperate with the first mix engagement mechanism for linearly and distally displacing the container holder into the housing when the manual knob is rotated, such that distal displacement of the container holder causes distal displacement of the container in relation to the plunger rod, whereby the plunger rod forces the distal stopper to be proximally displaced and thereby mixes the at least two substances.

2. The medicament delivery device of claim 1, further comprising a medicament delivery activation member slidably arranged in the housing and surrounding the container holder, the activation member having a proximal part with a contact part configured to be applied against a delivery site and protruding from the proximal end of the housing, and a second holding mechanism releasably engaged to the flexible holding mechanism when the plunger rod and the holding mechanism are in the pre-tensioned state.

3. The medicament delivery device of claim 2, wherein the activation member includes a locking mechanism arranged to be in contact with the proximal end of the mix member for preventing distal movement of the medicament delivery activation member until manual mixing has been performed.

4. The medicament delivery device of claim 3, wherein the container holder includes a release mechanism arranged to come in contact with the locking mechanism when the container holder has been distally displaced for releasing the locking mechanism and allowing distal displacement of the activation member.

5. The medicament delivery device of claim 4, further comprising an activation member force drive mechanism arranged between the second holding mechanism and a distal wall of the rotatable manual knob, wherein the activation member force drive mechanism is configured for pushing the medicament delivery activation member to an extended state after withdrawing the activation member from the delivery site, and the locking mechanism is configured for locking the activation member in the extended state when the locking mechanism passes over the release mechanism.

6. The medicament delivery device of claim 1, wherein the rotatable manual knob comprises a second holding mechanism releasably engaged to the flexible holding mechanism when the plunger rod and the holding mechanism are in the pre-tensioned state.

7. The medicament delivery device of claim 6, further comprising a medicament delivery activation mechanism arranged to the container holder and radially protruding through elongated slits on the housing; such that when the activation mechanism and thereby the container holder are proximally displaced, the flexible holding mechanism is disengaged from both the second holding mechanism and the first holding mechanism.

8. The medicament delivery device of claim 7, wherein the housing includes a first locking mechanism arranged to be in contact with the proximal end of the mix member for preventing proximal movement of the medicament delivery activation mechanism until manual mixing has been performed.

9. The medicament delivery device of claim 8, wherein the container holder includes a release mechanism arranged to come in contact with the first locking mechanism when the container holder is distally displaced for releasing the first locking mechanism and allowing proximal displacement of the activation mechanism.

10. The medicament delivery device of claim 7, further comprising a retraction force drive mechanism arranged between a first annular ledge of the mix member and a second annular ledge of the housing, wherein the retraction force drive mechanism is compressed when the activation mechanism is proximally displaced.

11. The medicament delivery device of claim 10, wherein the mix member includes a second locking mechanism arranged to come in contact with a corresponding third locking mechanism of a locking sleeve which is rotationally locked to both the rotatable manual knob and the mix member, for locking the activation mechanism in a retracted position within the housing when the activation mechanism is released after a medicament delivery and the compressed retraction force drive mechanism forces the mix member to be distally displaced.

12. The medicament delivery device of claim 1, wherein the medicament container holder includes a proximal attachment mechanism arranged to cooperate with a corresponding attachment mechanism of a delivery member.

13. The medicament delivery device of claim 1, wherein the multi-chamber medicament container is a syringe.

* * * * *